(12) United States Patent
Sengun et al.

(10) Patent No.: US 10,016,195 B2
(45) Date of Patent: Jul. 10, 2018

(54) SUTURE LEADER

(71) Applicant: DePuy Mitek, LLC, Raynham, MA (US)

(72) Inventors: Mehmet Z. Sengun, Canton, MA (US); David B. Spenciner, North Attleboro, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 30 days.

(21) Appl. No.: 14/966,758

(22) Filed: Dec. 11, 2015

(65) Prior Publication Data

US 2016/0095590 A1 Apr. 7, 2016

Related U.S. Application Data

(62) Division of application No. 13/623,290, filed on Sep. 20, 2012, now Pat. No. 9,247,936.

(51) Int. Cl.
*A61B 17/06* (2006.01)
*A61B 17/04* (2006.01)
(Continued)

(52) U.S. Cl.
CPC ...... *A61B 17/0485* (2013.01); *A61B 17/0401* (2013.01); *A61B 17/06166* (2013.01);
(Continued)

(58) Field of Classification Search
CPC .......... A61B 17/0401; A61B 17/06166; A61B 2017/0458; A61B 2017/06185; A61B 2017/0619; A61B 2017/444
See application file for complete search history.

(56) References Cited

U.S. PATENT DOCUMENTS

| 3,311,110 A | 3/1967 | Singerman et al. |
| 4,604,821 A | 8/1986 | Moser |

(Continued)

FOREIGN PATENT DOCUMENTS

| EP | 2422711 A2 | 2/2012 |
| WO | 2008048626 | 4/2008 |

OTHER PUBLICATIONS

European Search Report for Application No. 13185441.6 dated Jan. 20, 2014 (6 Pages).

(Continued)

*Primary Examiner* — Julie A Szpira

(57) ABSTRACT

Methods and devices are provided for securing tissue to bone. In general, a suture leader can have leading and trailing ends, and an inner passageway configured to receive a strand of suture therein. More specifically, the trailing end of the leader can be configured to receive the strand of suture therein to form an overlapping region of suture leader and suture. When the suture is positioned in the leader, an outer diameter of the leading end of the leader can be less than an outer diameter of the over lapping region. The leader can have a lower bending stiffness than the suture so that the leader can be more easily folded into a bend. In certain aspects, the suture leader can be formed from a substantially flexible, braided material so that the leader can be configured to contract when a pulling force is applied to the leader. In another embodiment, the suture leader can have a preformed crease configured to mate with a threading tool.

16 Claims, 11 Drawing Sheets

(51) Int. Cl.
*A61B 90/92* (2016.01)
*A61B 17/00* (2006.01)

(52) U.S. Cl.
CPC .... *A61B 90/92* (2016.02); *A61B 2017/00004* (2013.01); *A61B 2017/0412* (2013.01); *A61B 2017/0458* (2013.01); *A61B 2017/0619* (2013.01); *A61B 2017/06185* (2013.01)

(56) References Cited

U.S. PATENT DOCUMENTS

| | | | |
|---|---|---|---|
| 4,643,178 | A | 2/1987 | Nastari et al. |
| 4,781,191 | A | 11/1988 | Thompson |
| 5,358,498 | A | 10/1994 | Shave |
| 5,534,011 | A | 7/1996 | Greene, Jr. et al. |
| 5,865,836 | A | 2/1999 | Miller |
| 5,972,024 | A | 10/1999 | Northrup, III et al. |
| 6,203,572 | B1 * | 3/2001 | Johnson ............ A61F 2/08 606/108 |
| 6,602,290 | B2 | 8/2003 | Esnouf et al. |
| 7,892,256 | B2 | 2/2011 | Grafton et al. |
| 8,114,128 | B2 | 2/2012 | Cauldwell et al. |
| 8,133,257 | B2 | 3/2012 | Cook et al. |
| 8,517,073 | B2 | 8/2013 | Bogart et al. |
| 8,961,560 | B2 | 2/2015 | Avelar et al. |
| 9,247,936 | B2 | 2/2016 | Sengun et al. |
| 2006/0106423 | A1 * | 5/2006 | Weisel ............ A61B 17/0401 606/232 |
| 2007/0213770 | A1 | 9/2007 | Dreyfuss |
| 2008/0147119 | A1 | 6/2008 | Cauldwell et al. |
| 2008/0154286 | A1 | 6/2008 | Abbott et al. |
| 2009/0076544 | A1 | 3/2009 | DiMatteo et al. |
| 2009/0240104 | A1 | 9/2009 | Ogdahl et al. |
| 2010/0057113 | A1 | 3/2010 | Levin et al. |
| 2010/0160962 | A1 | 6/2010 | Dreyfuss et al. |
| 2012/0197294 | A1 * | 8/2012 | Martin ............ A61B 17/06166 606/228 |
| 2014/0081320 | A1 | 3/2014 | Sengun et al. |
| 2014/0081322 | A1 | 3/2014 | Sengun et al. |
| 2014/0081323 | A1 | 3/2014 | Hawkins |
| 2014/0081325 | A1 | 3/2014 | Sengun |

OTHER PUBLICATIONS

U.S. Appl. No. 13/623,258, filed Sep. 20, 2012 (32 Pages).
U.S. Appl. No. 13/623,449, filed Sep. 20, 2012 (44 Pages).
U.S. Appl. No. 13/623,467, filed Sep. 20, 2012 (29 Pages).
European Search Report for Application No. 16181322.5 dated Mar. 13, 2017.

* cited by examiner

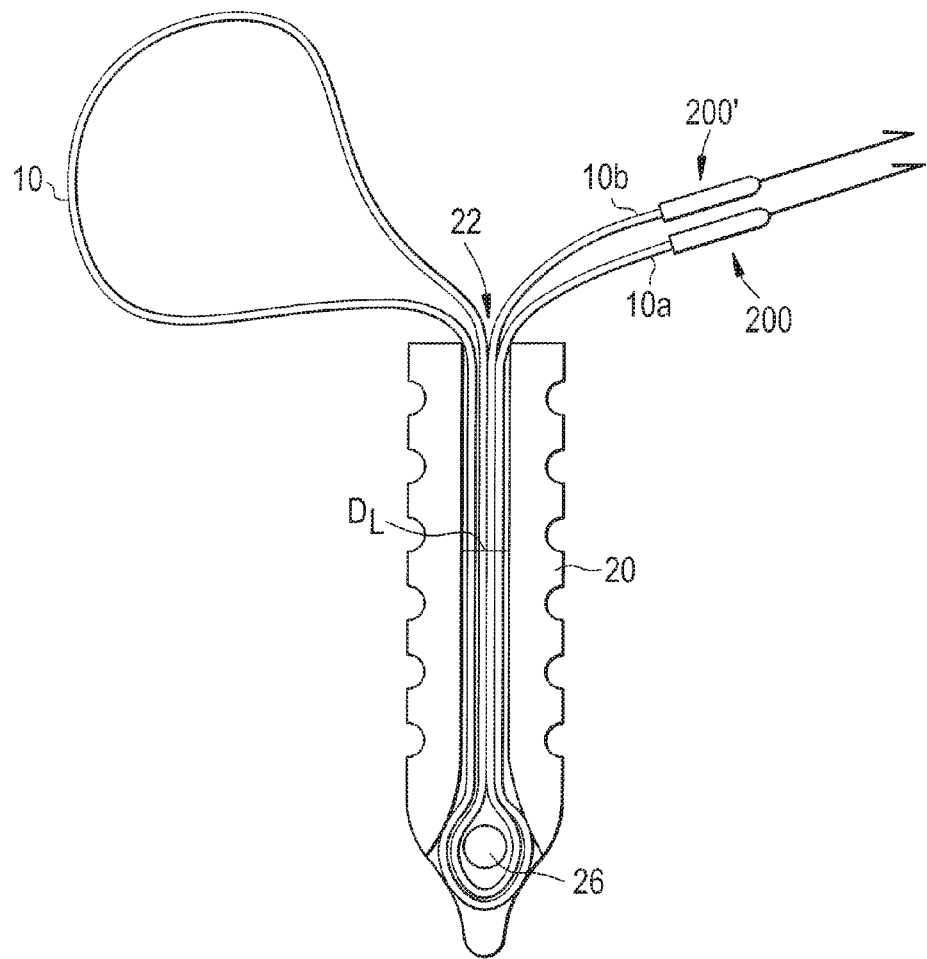

SUTURE LEADER

CROSS REFERENCE TO RELATED APPLICATIONS

This application is a divisional of U.S. application Ser. No. 13/623,290 filed Sep. 20, 2012, and entitled "Suture Leader," which is hereby incorporated by reference in its entirety.

FIELD OF THE INVENTION

The present disclosure relates to devices and methods for attaching soft tissue to bone.

BACKGROUND OF THE INVENTION

The complete or partial detachment of ligaments, tendons and/or other soft tissues from their associated bones within the body are relatively commonplace injuries, particularly among athletes. Such injuries are generally the result of excessive stresses being placed on these tissues. By way of example, tissue detachment may occur as the result of an accident such as a fall, over-exertion during a work-related activity, during the course of an athletic event, or in any one of many other situations and/or activities. In the case of a partial detachment, the injury will frequently heal itself, if given sufficient time and if care is taken not to expose the injury to further undue stress. In the case of complete detachment, however, surgery may be needed to re-attach the soft tissue to its associated bone or bones.

Numerous devices are currently available to re-attach soft tissue to bone. Examples of such currently-available devices include screws, staples, suture anchors, and tacks. In soft tissue re-attachment procedures utilizing screws, the detached soft tissue is typically moved back into its original position over the bone. Then the screw is screwed through the soft tissue and into the bone, with the shank and head of the screw holding the soft tissue to the bone. Similarly, in soft tissue re-attachment procedures utilizing staples, the detached soft tissue is typically moved back into its original position over the bone. Then the staple is driven through the soft tissue and into the bone, with the legs and bridge of the staple holding the soft tissue to the bone.

In soft tissue re-attachment procedures utilizing suture anchors, an anchor-receiving hole is generally first drilled in the bone at the desired point of tissue re-attachment. A suture anchor is then deployed in the hole using an appropriate installation tool. This effectively locks the suture, with soft tissue attached thereto.

While suture anchors provide an effective, minimally-invasive technique for soft tissue repair, it is desirable to utilize an anchor having a small diameter so as to avoid unnecessary trauma. The size of the anchor, however, can be limited by the size of the suture and/or the bending stiffness of the suture. Typically, a single strand of repair suture is folded and trailing ends of the suture are attached to a threader loop, which is used to pull the folded suture into the anchor. When a folded suture is used, the cannulated portion of the anchor must be large enough to accommodate at least two times the thickness of the repair suture. The bending stiffness of the repair suture used can also limit the size of the anchor. For example, high strength suture can have a greater bending stiffness than other types of suture and this can make it difficult to bring legs of the suture together to form a 180° fold, especially near the location of the bend. Because a width at the bend is larger than a width of two legs of the suture, it can be difficult to fit the bend in a lumen in the anchor. This in turn restricts the ability to reduce the size of the anchor.

Accordingly, there remains a need for improved methods and devices for attaching soft tissue to bone.

SUMMARY OF THE INVENTION

Various surgical devices are provided herein. In one embodiment, a surgical device is provided that includes at least one suture strand and a biocompatible suture leader. The suture leader can have a first terminal end portion that is mated to a terminal end portion of the at least one suture strand. The suture leader can have an outer diameter along at least a portion of a length thereof that is less than a maximum outer diameter of the at least one suture strand. The suture leader can further include a pre-formed crease therein such that the suture leader is bent when it is in a resting state.

The device can vary in a number of ways. For example, the first terminal end portion of the suture leader can be configured to collapse around the terminal end portion of the at least one suture strand when a pulling force is applied to the suture leader. For another example, the terminal end portion of the at least one suture strand can be disposed within an inner passageway in the first terminal end portion of the suture leader. The suture leader can further include a second terminal end portion having an outer diameter that is preferably less than one half an outer diameter of the at least one suture strand. In certain aspects, the suture leader can be detachably mated to the at least one suture strand. The at least one suture strand can include a single suture strand having first and second terminal end portions that are received within the first terminal end portion of the suture leader. In other aspects, the at least one suture strand can include first and second suture strands, and a first terminal end of the first suture strand and a second terminal end of the second suture strand can be received in the first terminal end portion of the suture leader.

In another embodiment, a suture can include a first length of biocompatible suture strand and a first length of biocompatible suture leader. The suture strand can have leading and trailing ends. The suture leader can have a lumen extending at least partially therethrough and originating at a trailing end thereof. The suture leader can have an outer diameter along at least a portion thereof that is less than a maximum outer diameter of the first length of suture strand. The leading end of the first length of suture can be disposed within the lumen in the trailing end of the suture leader such that a force applied to a leading end of the suture leader causes the trailing end of the suture leader to contract and engage the leading end of the suture strand.

The suture can vary in other ways. For example, the suture can include a second length of biocompatible suture strand having a leading end disposed within the lumen of the suture leader. The suture leader can include a pre-formed hook formed therein. The trailing end of the suture leader can be configured to contract around the suture strand when a tensile force is applied to the suture leader. In certain aspects, the suture leader can have a braided structure. In other aspects, the suture leader can have a color contrasted from a color of the suture strand to visually distinguish the suture leader from the suture strand. The suture leader and the suture strand can be fixedly coupled at one or more discrete locations.

A method for attaching tissue to bone is also provided, and can include threading suture into a suture anchor. In one embodiment, the method can include positioning a threader loop within a crease pre-formed in a suture leader such that the suture leader is hooked onto the threader loop, and pulling the threader loop to pull the suture leader through a lumen in a suture anchor. The suture leader can have a suture attached to a first trailing end thereof, and the suture leader can collapse around the suture as the suture leader is pulled through the suture anchor.

The surgical method can include a variety of modifications. For example, pulling the suture leader can cause at least a portion of the suture leader to radially collapse around the suture. Pulling the threader loop can include pulling the threader loop distally through the lumen, around a suture-receiving member in the suture anchor, and proximally through the lumen. The surgical method can also include detaching the suture leader from the suture strand after the suture leader is pulled through the suture anchor. Prior to pulling the threader loop through the suture anchor, the threader loop can be positioned within a crease pre-formed in a second suture leader, the second suture leader being attached to a second trailing end of the suture. Pulling the threader loop can decrease outer diameters of the first and second suture leaders such that the first and second suture leaders are dimensioned to pass through an eyelet formed in the suture anchor. The suture leader can also have a first suture and a second suture attached to the first trailing end thereof.

BRIEF DESCRIPTION OF DRAWINGS

This invention will be more fully understood from the following detailed description taken in conjunction with the accompanying drawings, in which:

FIG. 12 is a cross-sectional view of the anchor of FIG. 11 with the suture threaded completely through the anchor and the leaders positioned outside of the anchor.

DETAILED DESCRIPTION OF THE INVENTION

Figure 1:
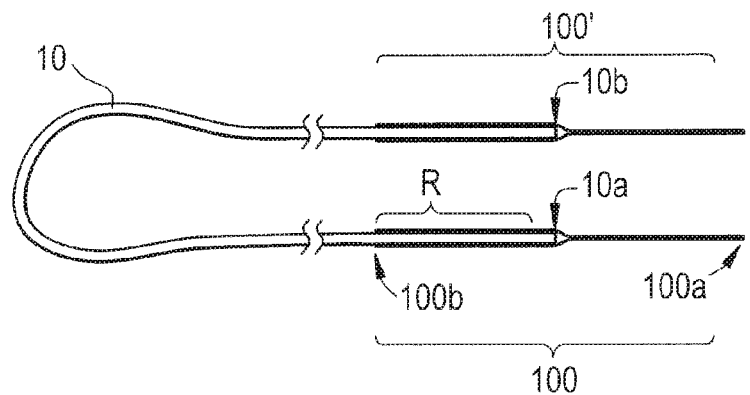
FIG. 1 is perspective, semi-transparent view of two suture leaders mated with a suture, according to one exemplary embodiment.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The figures provided herein are not necessarily to scale. Still further, to the extent arrows are used to describe a direction a component can be tensioned or pulled, these arrows are illustrative and in no way limit the direction the respective component can be tensioned or pulled. A person skilled in the art will recognize other ways and directions for creating the desired tension. Likewise, while in some embodiments movement of one component is described with respect to another, a person skilled in the art will recognize that other movements are possible. Additionally, a number of terms may be used throughout the disclosure interchangeably but will be understood by a person skilled in the art.

Various devices and methods are provided for threading a suture through a suture anchor, and for anchoring suture to bone. In general, the present invention provides a suture leader that is configured to mate with an end of at least one suture, and that can facilitate loading of at least one suture onto a suture anchor. For example, in one embodiment the suture leader can have an inner passageway sized to receive one or more ends of one or more sutures. In certain aspects, a leading end of the leader can include a bent or hooked end portion that is configured to mate with a suture threading tool, such as a threader loop. In use, the suture leader can be mated to one or more sutures, and the leader can be folded around or hooked onto the threading tool. Because the leader can have a low bending stiffness relative to the bending stiffness of the suture(s), the folded leader can have a smaller width near the bend than if the suture were directly folded around the threader and then pulled through the anchor. Alternatively, the hooked end of the suture leader can provide a reduced-width region, as compared to a bent suture, that facilitates passage through an anchor. A pulling force can be applied to the suture leader to cause an overlapping region of the leader to contract around the suture(s) and provide a smooth transition between the suture(s) and the leader. The leader can guide the suture through the anchor until the suture is threaded completely through the anchor and the leader is positioned outside of the anchor. In one embodiment, the suture leader can be detached from the suture(s) after the suture(s) has been threaded onto the anchor, such as by sliding the suture leader off the suture(s).

FIG. 1 illustrates an exemplary embodiment of first and second suture leaders 100, 100' mated to first and second ends of a single strand of suture 10. Though reference is made to suture leader 100, suture leader 100' can have the same features. In general, the suture leader 100 can have an elongate shape and can have first and second terminal ends 100a, 100b. The suture leader 100 can also have an inner passageway 102 extending through all or a portion thereof for receiving one of more ends of a suture, such as a first end 10a of the suture 10. The first/leading end 100a of the suture leader can facilitate loading of the suture 10 onto an anchor (not shown) by leading the suture 10 into the anchor, as will be discussed in greater detail below. A person skilled in the art will appreciate that the suture leader can be configured to mate to or receive any number of ends of one or more sutures.

Figure 2A:
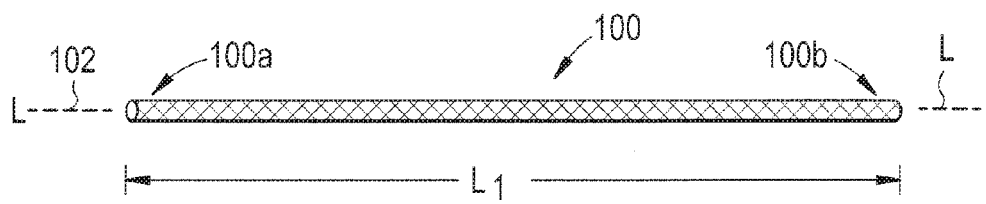
FIG. 2A is a side view of the suture leader of FIG. 1.
Figure 2B:
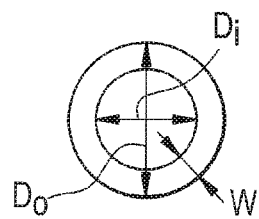
FIG. 2B is a cross-sectional view of the suture leader of FIG. 2A, taken along an axis perpendicular to longitudinal axis L.

The suture leader 100 can have various sizes, shapes, and configurations. FIG. 2A illustrates the suture leader 100 without a suture disposed therein. As shown, the suture leader 100 can have a substantially cylindrical shape with the inner passageway 102 extending along a longitudinal axis L thereof. The inner passageway 102 can extend along a portion of the suture leader 100 or along an entire length of the leader 100, but preferably the inner passageway 102 originates at a terminal end portion of the leader 100, e.g., at terminal end 100a as shown. A person skilled in the art will appreciate that the suture leader can have other cross-sectional shapes, such as ovular, square, rectangular, etc. FIG. 2B is a cross-sectional view of the suture leader 100 and shows an inner diameter $D_i$, an outer diameter $D_o$, and a wall thickness W. In general, the suture leader 100 can have a relatively thin wall thickness W such that when a suture is disposed therein, the outer diameter of the suture leader along the region overlapping the suture is smaller than twice a diameter of the suture it receives. That is, the wall thickness W should be thin enough so that of the suture plus two times the added wall thickness W from the suture leader 100 is still be smaller than a width of a folded suture 10, as will be discussed below. A length of the suture leader $L_1$ can be selected based on the particular surgical procedure to be performed, but in one embodiment the length $L_1$ can be in the range of about 70 mm to 250, such as about 200 mm, as measured from terminal end to terminal end when the suture leader 100 is in a linear configuration.

The suture leader 100 can have various mechanical properties that can facilitate use of the suture leader for loading a suture onto a suture anchor. In one embodiment, the suture leader 100 can be relatively stiff along its length, but bendable to allow for ease of threading the leader 100 through a bone anchor. In another embodiment, the suture leader 100 can be substantially flexible along its length. The manufacturing techniques and/or the material(s) used can be selected to achieve a desired flexibility. By way of non-limiting example, such material can include high molecular weight polyethylene, polyester, polyethylene terephthalate (PET), polyether ether ketone (PEEK), or a blend of any combination of these materials. During manufacturing, filaments and/or fibers can be braided, twisted, and/or weaved together to form a leader having an inner passageway, also referred to as a hollow core. For example, FIG. 2A illustrates the suture leader 100 with a woven or braided structure and having the inner passageway extending through its entire length $L_1$. In another embodiment, a first portion of the suture leader can have a braided structure with the hollow core/inner passageway extending therethrough, and a second portion of the leader can be substantially solid. Alternatively, the suture leader can be formed from a solid material, and the core of the suture leader can be partially or entirely removed. By way of non-limiting example, the suture leader can be formed from commercially available suture, such as ETHIBOND #0 manufactured by Ethicon, Inc. of Somerville, N.J.

Figure 3A:
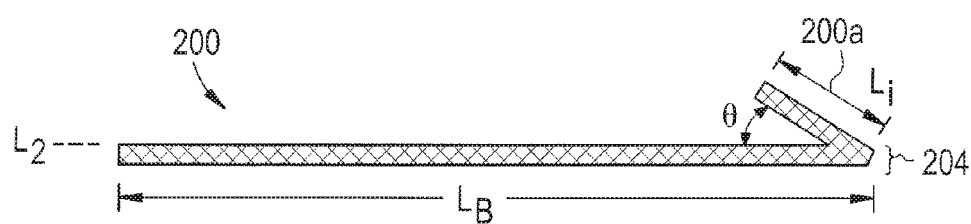
FIG. 3A is another embodiment of a suture leader having a bent terminal end portion.

The suture leader can have a variety of other features. Another embodiment of a suture leader 200 is illustrated in FIG. 3A. As shown, an end portion of the suture leader 200 can have an engagement feature, such as a pre-formed hook, to facilitate engagement to a suture or a threader loop. Various techniques can be used to form the hook. By way of non-limiting example, the suture leader can include a fold or crease formed therein such that when the suture leader 200 is in a resting configuration, the end of the suture leader can be bent or hooked. In particular, a terminal end 200a of the suture leader 200 can be angularly offset from a longitudinal axis $L_2$ of the suture leader 200 by an angle θ so that the leader 200 can be hooked onto a threader (not shown). By way of non-limiting example, the angle θ can be in the range of about 0-90°. As will be appreciated by a person skilled in the art, the crease 204 can be formed at various locations on the suture leader 200. The location of the crease 204 relative to the terminal end 200a of the leader 200 can be at a distance that ensures that the end can hook onto a threader. For example, the crease can be at a position such that the end portion has a length $L_C$ that can be in the range of about 12 mm to 100 mm and a body of the leader can have a length $L_B$ that can be in the range of about 25 mm to 300 mm.

The crease 204 can be formed using various manufacturing techniques, such as compression or heat setting or by applying biocompatible glue and/or other bonding material known in the art, or by other techniques, either separately or in combination. Thus, the crease 204 can be made strong enough to substantially maintain its shape when it is passed through tissue.

Figure 3B:
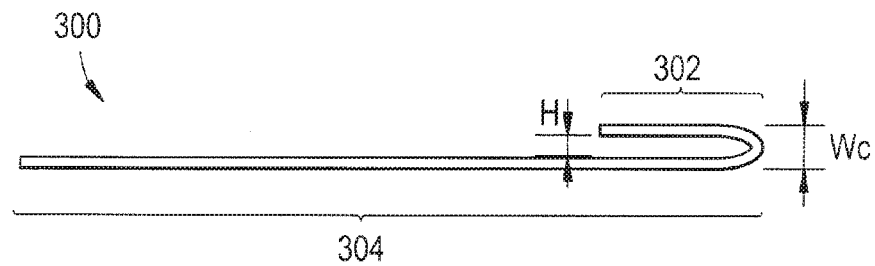
FIG. 3B is another embodiment of a suture leader having a curved terminal end portion.

In another embodiment shown in FIG. 3B, a suture leader 300 can have a terminal end that is curved or has a J-shaped hook. For example, the leader 300 can have a curved terminal end portion 302, rather than a sharp bend or crease. The terminal end portion 302 of the leader 300 can be spaced at a distance away from a body 304 of the leader 300 to define a height H. The leader 300 can be formed from a solid material, such as monofilament suture, that can substantially retain its shape even when the leader 300 is passed through tissue.

Figure 4A:
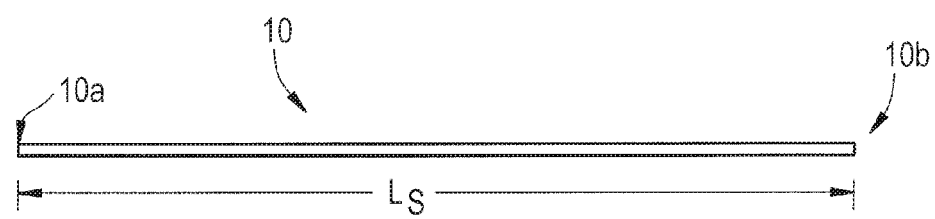
FIG. 4A is a perspective view of an exemplary suture configured to be received within a suture leader.
Figure 4B:
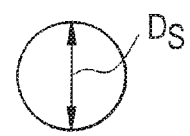
FIG. 4B is a cross-sectional view of the suture of FIG. 4A.

Leaders 100, 200, and 300 can be used with any suture and with any number of sutures. While the suture 10 can have various sizes, shapes, and configurations, FIG. 4A illustrates one embodiment of a suture 10 that includes the first and second terminal ends 10a, 10b with a length $L_S$ therebetween. The suture 10 can have a length $L_S$ such that it can be threaded through tissue and through a bone anchor, with terminal ends extending from the bone anchor. The suture 10 can have an outer diameter $D_S$, as shown in FIG. 4B that can vary. By way of non-limiting example, the outer diameter $D_S$ of the suture 10 can be in the range of about 0.15 mm to 0.7 mm, and preferably about 0.5 mm to 0.6 mm. This corresponds to sutures ranging from size #4-0 to size #5, and preferably size #2. The suture 10 can include an inner passageway (not shown) extending along a longitudinal axis of the suture 10, or as in the illustrated embodiment, the suture 10 can be substantially solid along its length $L_S$. The suture 10 can be formed from a biocompatible material, and the material can be absorbable, partially-absorbable, or non-absorbable depending on the particular surgical procedure. For example, non-absorbable suture can be used in surgical procedures that require a strong amount of fixation in order to maintain contact between tissue and adjacent bone. By way of non-limiting example, the suture 10 can be a high strength suture, such as ORTHOCORD #2 manufactured by Ethicon, Inc. of Somerville, N.J.

The suture 10 and suture leader 100 can have other features. Though reference is made to suture leader 100, suture leaders 200, 300 can have any combination of the features described herein. In one embodiment, the suture 10 and leader 100 can be visually distinct. For example, the suture 10 can be formed from a first color and the leader 100 can be formed from a second color to help a user visually identify the end of an overlapping region of the leader 100 from the suture 10. This can be accomplished by dying or otherwise marking the suture 10 and/or the suture leading 100 during manufacturing. Alternatively, the suture and suture leader can each be braided from filaments of differing color, and/or using different pick counts to produce distinct patterns. Non-limiting examples of sutures having different pick counts are discussed in U.S. patent application Ser. No. 13/623,467, filed on Sep. 20, 2012, and entitled "Methods and Devices for Threading Sutures," which is hereby incorporated by reference in its entirety.

Figure 5A:
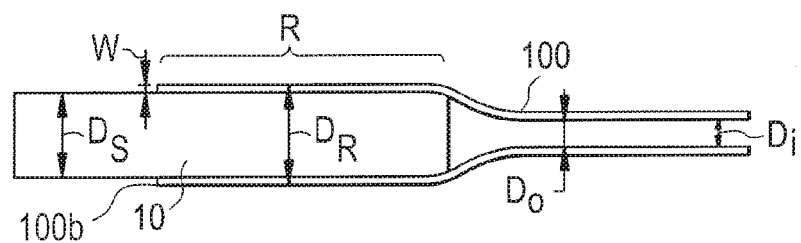
FIG. 5A is a partially transparent, side view of the suture leader and suture of FIG. 1, showing the overlapping region of suture leader and suture.

In use, the first end 10a of the suture 10 can be received in the trailing, second end 100b of the suture leader 100 to form an overlapping region R, as shown in FIG. 5A. The overlapping region R can have any length, such as a length in the range of about 50 mm to 160 mm, to ensure sufficient contact between the suture 10 and the suture leader 100. The relative diameters of the suture, the leader, and the overlapping region can vary, and the relative sizing can apply to the leaders 100, 200, and 300. When the suture 10 is positioned in the leader 100, as shown in FIG. 5A, the outer diameter $D_R$ of the overlapping region R is defined by the outer diameter $D_S$ of the suture 10 plus twice the wall thickness W of the suture leader 100. In one embodiment, the outer diameter $D_R$ of the overlapping region R can be slightly larger than the outer diameter $D_S$ of the strand of suture 10. Preferably, the outer diameter $D_R$ of the overlapping region is less than twice the diameter $D_S$ of the suture. As shown, the outer diameter $D_o$ of the leading end 100a of the leader can be equal to or smaller than the outer diameter $D_S$ of the suture strand 10. More preferably, the outer diameter $D_o$ of the leading end 100a is less than half the outer diameter $D_R$ of the overlapping region R. In this way, the reduced diameter of the leading end 100a can counteract the added wall thickness W in the overlapping region R.

The suture 10 can be positioned within the leader 100 using various techniques. Referring back to FIG. 2A, when the suture leader 100 does not have a suture disposed therein, the leader 100 can have an inner diameter that can be substantially constant along its length $L_1$. As shown in FIG. 5A, when the leader 100 has the suture 10 positioned therein, the leader 100 can have inner diameter $D_i$ at the leading end 100a that is less than the outer diameter $D_S$ of the suture 10. Accordingly, the inner diameter of the leader 100 can thus be expanded at the overlapping region R, such as by compressing the leader 100 in a longitudinal direction, so that the leader 100 can be sized to receive the suture therein. This can expand the outer diameter of the leader 100 such that the diameter $D_R$ of the leader 100 at the trailing, second end 100b is greater than the outer diameter $D_o$ at the leading, first end 100a. Typically, the suture 10 can be mated with the leader 100 during the manufacturing process by sliding the suture 10 into the lumen in the trailing end 100b of the leader 100.

Figure 5B:
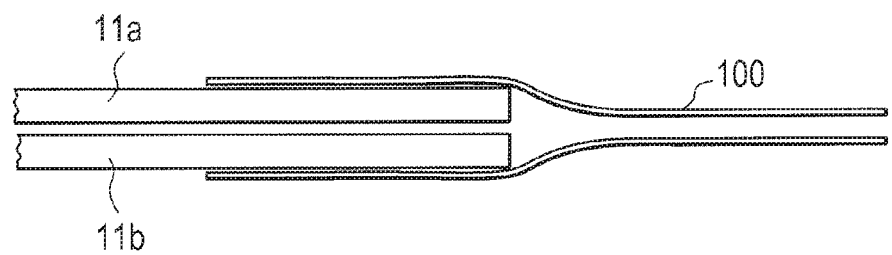
FIG. 5B is a partially transparent, side view of the suture leader of FIG. 1 having first and second terminal ends of suture received therein.

While FIG. 5A illustrates a suture leader having a single strand of suture therein, a person skilled in the art will appreciate that the suture leader can be configured to receive any number of suture strands therein. By way of example, FIG. 5B illustrates first and second terminal ends 11a, 11b of suture disposed within and mated to suture leader 100. The terminal ends 11a, 11b can be ends of the same suture, or ends of two different sutures. While not shown, a folded portion of one or more sutures can also be received in the suture leader.

Figure 5C:
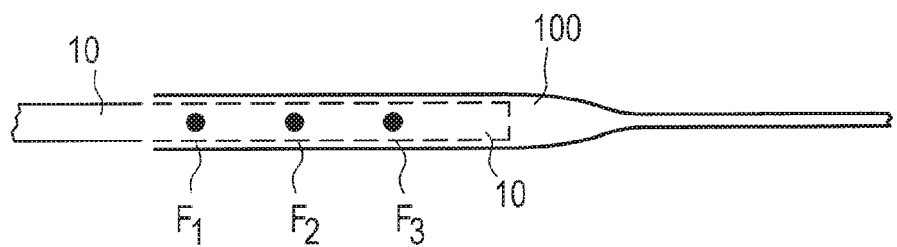
FIG. 5C is a partially transparent, side view of the suture leader and suture of FIG. 1, showing a plurality of fixation points.

In general, the suture leader 100 and the suture 10 can be temporarily or permanently mated together using various techniques. For example, in one embodiment the suture leader 100 can radially contract or compress around an outer circumference of the suture 10 when an axial pulling force is applied to the suture leader. This can prevent the suture 10 from unintentionally being pulled out from the suture leader 100. When tension is applied to the leader 100 by pulling on the leading end 100a of the leader, the braided configuration of the leader 100 will be pulled axially, thus tightening the braid and increasing the contracting force around the suture 10. The leader 100 can function as a Chinese finger trap in that the applied tension can both increase a length of the leader and decrease inner and outer diameters of the leader 100. In another embodiment, the mating between the suture leader 100 and the suture 10 can be supplemented at one or more discrete locations along the overlapping region. For example, FIG. 5C depicts the leader 100 and suture 10 with evenly spaced fixation points $F_1$, $F_2$, and $F_3$. The fixation points $F_1$, $F_2$, and $F_3$ can be made using various techniques known in the art, such as heat treatment, spot welds, etc, and any number of fixation points can be positioned at any location on the overlapping region R. Additionally or alternatively, fibers or filaments of the suture 10 and the leader 100 can be spliced together at various locations to form temporary or permanent fixation points.

Figure 6:
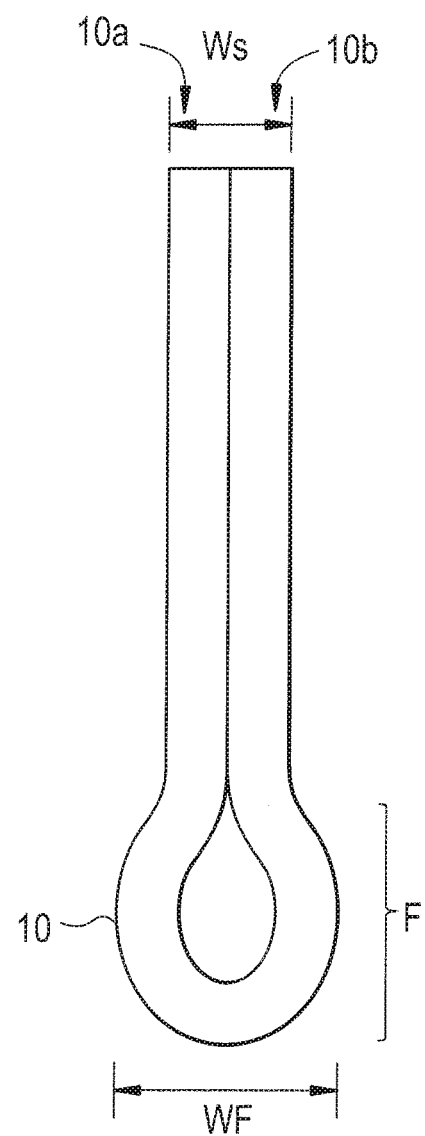
FIG. 6 is a perspective view of a suture in a folded configuration with a wide bent portion compared with the width near the first and second ends.

As previously mentioned, the bending stiffness of a suture can make it difficult to thread a suture onto an anchor. FIG. 6 illustrates one example of this concept, showing the suture 10 in a folded configuration. Because the suture 10 can have a high bending stiffness, opposed sides of the suture cannot be brought together to form a 180° fold. Rather, a folded portion F of the suture 10 has a width $W_F$ that is greater than a combined width $W_S$ of the suture legs. Because the folded portion F is typically pulled into an anchor before the first and second ends 10a, 10b, the suture 10 occupies a larger space than if it could achieve the 180° fold. A leader can thus be used in combination with the suture 10 to avoid the need to fold the suture for threading it into the anchor, as will be discussed.

Figure 7:
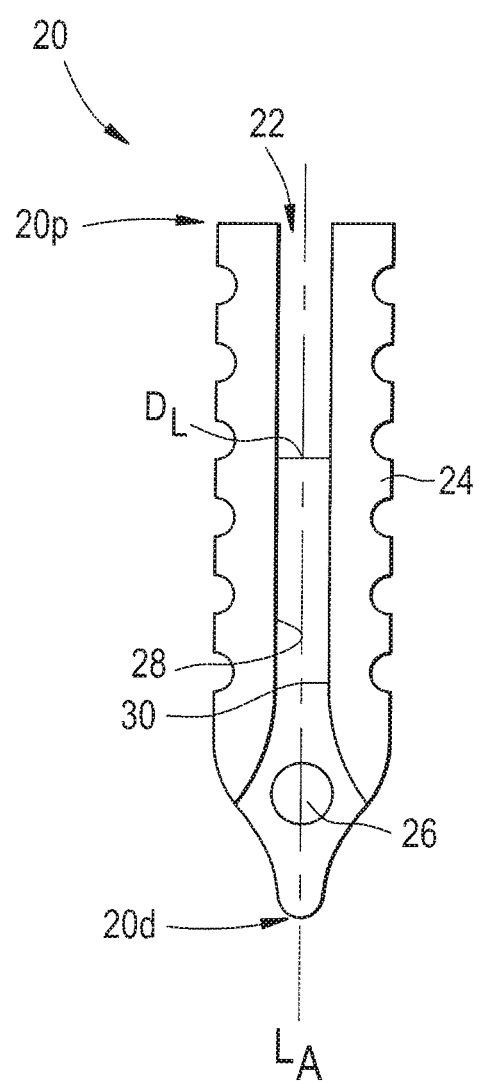
FIG. 7 is a cross-sectional view of one embodiment of an anchor configured to receive the suture leader and strand of suture of FIG. 1 therein.

FIG. 7 illustrates one exemplary embodiment of a cannulated suture anchor 20 for anchoring tissue to bone. As shown, the suture anchor 20 is in the form of a generally elongate body having proximal and distal ends 20p, 20d with an inner lumen 22 extending therethrough. In one embodiment, the inner lumen 22 can have a substantially cylindrical shape defining an inner diameter $D_L$. At least one bone-engaging surface feature 24 can be formed on at least a portion of an external surface thereof for engaging bone. The suture anchor 20 can also include a suture-receiving member 26 disposed within the inner lumen 22 adjacent to the distal end 20d of the suture anchor 20. The suture-receiving member 26 is adapted to receive one or more sutures therearound such that the suture(s) can extend around the suture-receiving member 26 and trailing ends of the suture(s) can extend through the inner lumen 22 and out of the proximal end 20p of the suture anchor 20.

The body of the suture anchor 20 can have a variety of configurations, shapes, and sizes. In an exemplary embodiment, the anchor 20 is configured to be implanted within a bone tunnel formed in bone, and more preferably it has a size and shape that allows it to be fully engaged through the thickness of the cortical bone. In the illustrated embodiment the body has a generally elongate cylindrical shape with a blunt or rounded distal end 20d to facilitate introduction of the anchor 20 into a bone tunnel. The proximal end 20p of the body can be head-free, and the cannulated body can be configured to allow a driver to be inserted into the inner lumen to drive the suture anchor into bone. In another embodiment, the proximal end 20p of the body can have a head for mating with a driver for driving the anchor 20 into bone. As indicated above, the suture anchor 20 can also include one or more bone-engaging surface features 24 formed thereon and adapted to engage bone. While various surface features can be used, such as teeth, ridges, protrusions, etc., in an exemplary embodiment the body can include one or more threads extending therearound.

As previously indicated above, the suture anchor 20 can also include a suture-receiving member formed therein. The suture-receiving member 26 can have a variety of configurations, but in an exemplary embodiment it is adapted to seat one or more sutures that extend through the inner lumen 22 of the anchor 20. As shown in FIG. 7, the suture-receiving member 26 is in the form of a post that extends transversely across the inner lumen 22 and between opposed inner sidewalls 28, 30 of the suture anchor. The angular orientation of the suture-receiving member 26 relative to a longitudinal axis $L_A$ of the inner lumen 22 can vary, but in an exemplary embodiment the suture-receiving member 26 extends substantially perpendicular to the longitudinal axis $L_A$ of the inner lumen 22. The location of the suture-receiving member 26 can also vary, but in an exemplary embodiment the suture-receiving member 26 is positioned at or adjacent to the distal end 20d of the suture anchor 20. In the embodiment shown in FIG. 7 the suture-receiving member 26 is located just proximal to the distal-most end 20d of the suture anchor 20 so as to form a suture-seating groove in the distal-most end 20d of the suture anchor 20. This recessed configuration of the suture-receiving member 26 can allow a suture(s) disposed around the suture-receiving member 26 to sit flush or sub-flush with the distal end 20d of the suture anchor 20 such that the suture(s) will not interfere with insertion of the suture anchor 20 into bone. A person skilled in the art will appreciate that the suture-receiving member can be integrally formed with the suture anchor, i.e., the suture anchor and suture-receiving member can be molded as a single unit or formed from a single piece of material, or the suture-receiving member can be fixedly or removably mated to the suture anchor. Additionally, the suture-receiving member can have other configurations, such as an eyelet that can receive the suture 10 and leader 100 therethrough. Non-limiting examples of suture anchors and deploying suture anchors into bone are described in further detail in U.S. app. Ser. No. 11/555,545 entitled "Cannulated Suture Anchor" filed Feb. 1, 2006, now U.S. Pat. No. 8,114,128, U.S. app. Ser. No. 11/855,670 entitled "Dual Thread Cannulated Suture Anchor" filed Sep. 14, 2007, U.S. app. Ser. No. 10/615,625 entitled "Bioabsorbable Suture Anchor System For Use In Small Joints" filed Jun. 27, 2003, now U.S. Pat. No. 8,133,257, U.S. patent application Ser. No. 13/623,258, filed on Sep. 20, 2012, and entitled "Anti-Backup Suture Anchor," and U.S. patent application Ser. No. 13/623,449, filed on Sep. 20, 2012 and entitled "Self-Cinching Suture Anchors, Systems, and Methods," all which are hereby incorporated by reference in their entireties.

The devices described above can be used to perform a surgical procedure for attaching tissue to bone, e.g. anterior cruciate ligament (ACL) repair, rotator cuff repair, etc. In an exemplary embodiment, a procedure including implantation of the anchor can be a minimally invasive procedure, but as will be appreciated by a person skilled in the art, the implants discussed herein also have application in open surgical instrumentation as well as application in robotic-assisted surgery. Though reference is made to suture 10 and suture leader 100, the devices shown are exemplary and the method can be performed with any number and any embodiment of a suture and a leader. For example, while some of the embodiments show a single suture leader mated with one terminal end of the suture, first and second ends of the suture can each have a different suture leader mated thereto or first and second ends of the same or different sutures can be disposed within a single leader. Additionally, the suture leader 100 can be substituted or interchanged with the suture leaders 200, 300 described above.

As one skilled in the art will appreciate, the procedure usually begins by preparing the patient for surgery and making one or more appropriately sized incisions at a desired location. In a minimally invasive procedure, one or more cannulas can be positioned in the incisions to provide access to the surgical site. One skilled in the art will also understand that one or more viewing devices, e.g., scopes, can be placed in one of the incisions to allow medical personnel to view the surgical site from outside the body.

Once the patient is prepared for surgery, a length of suture 10 can be inserted into the patient's body and through tissue to be surgically reattached to bone. When a combination suture and suture leader is used, the leading end of the suture leader can be inserted through the tissue directly using a tool, such as a needle. The leader can be used to pull the suture coupled thereto through the tissue. Alternatively, the suture can be threaded through the tissue and then coupled to the suture leader, e.g., by passing the leading end of the suture into the lumen in the trailing end of the suture leader. One skilled in the art will appreciate that the suture and/or leader can be passed through the tissue using any known surgical technique, such as by mattress and cinch loop methods. With the suture and leader so positioned, a bore, bone hole, or bone tunnel, generally referred to herein as a "bone hole," can be formed in bone of the patient. The bone hole can be pre-formed, such as by using a drill, an awl, a punch instrument, etc., as will be appreciated by a person skilled in the art. Alternatively, the bone hole can be formed simultaneously with advancement of a suture anchor into the bone and simultaneously with threadable engagement of the anchor therewith, such as by using a self-awling or self-tapping driver and/or self-awling or self-tapping anchor. The bone hole can extend fully through cortical bone to allow the suture anchor to be fully engaged through the thickness of the cortical bone. The bone tunnel can also extend into cancellous bone located underneath the cortical bone. The suture anchor can be deployed in the bone hole before or after suture leader is threaded or loaded onto the suture anchor. With the suture and/or leader(s) threaded through tissue, the terminal ends can extend outside of the body. The suture and the leader can be threaded onto the anchor, either before or after the anchor is implanted in bone.

Figure 8:
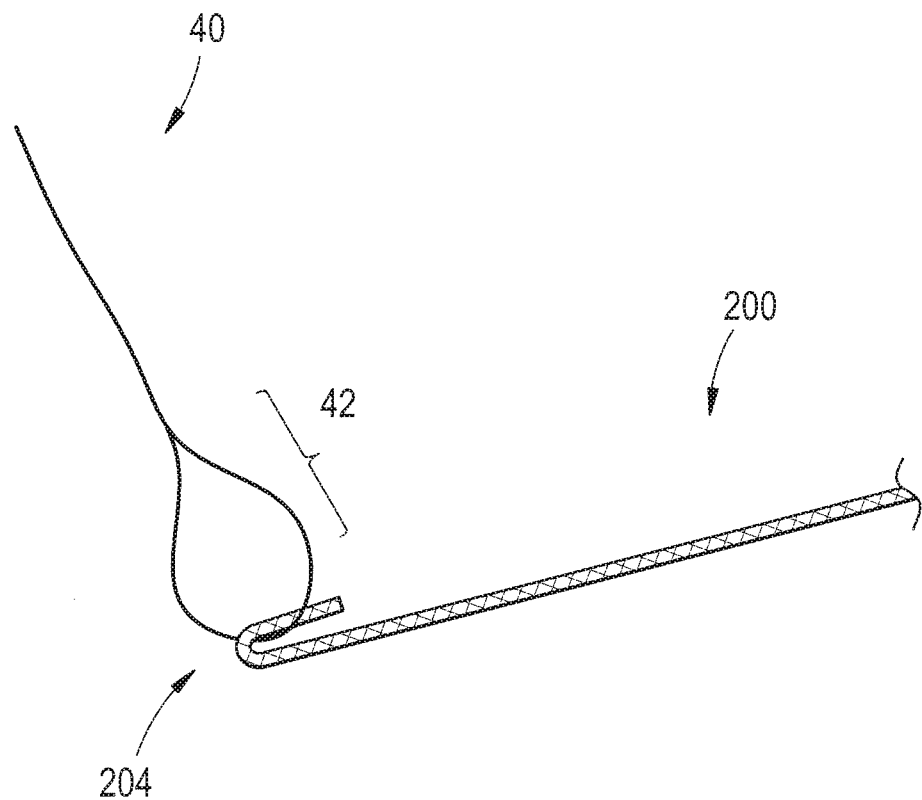
FIG. 8 is a perspective view of the suture leader of FIG. 3A having a first end mated to a threader loop.
Figure 9:
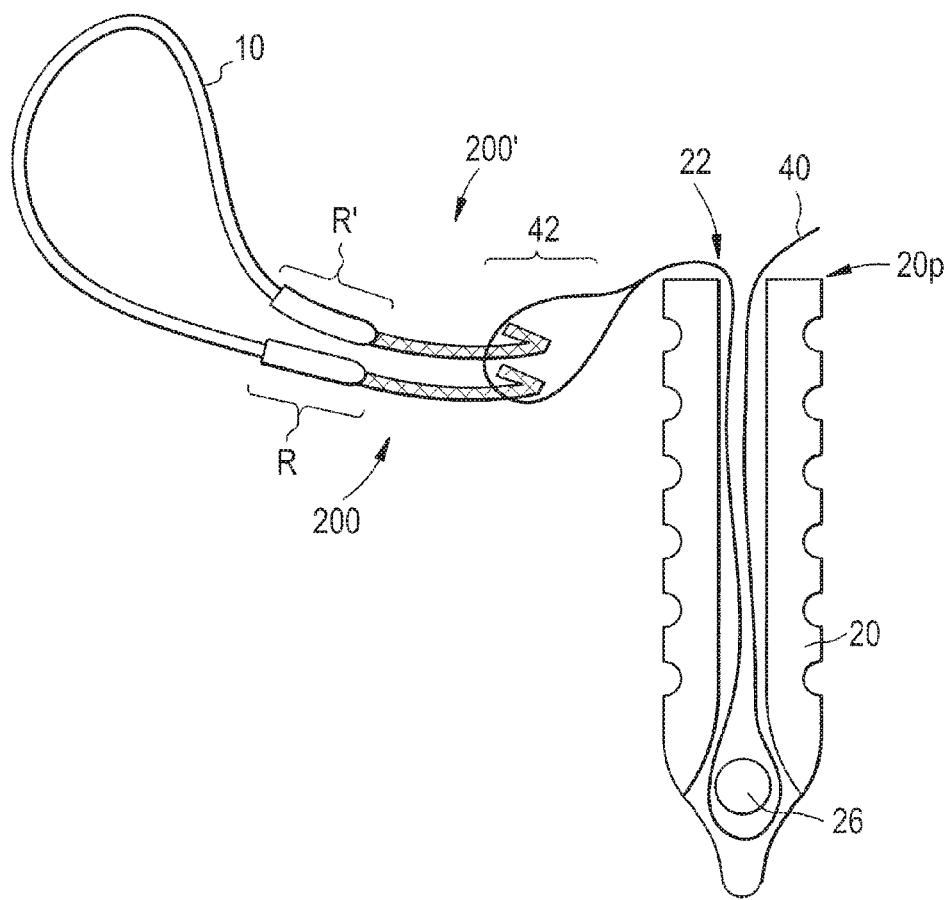
FIG. 9 is a cross-sectional view of the anchor of FIG. 7 with a threader loop extending therethrough and mated with bent terminal ends of two suture leaders.
Figure 10:
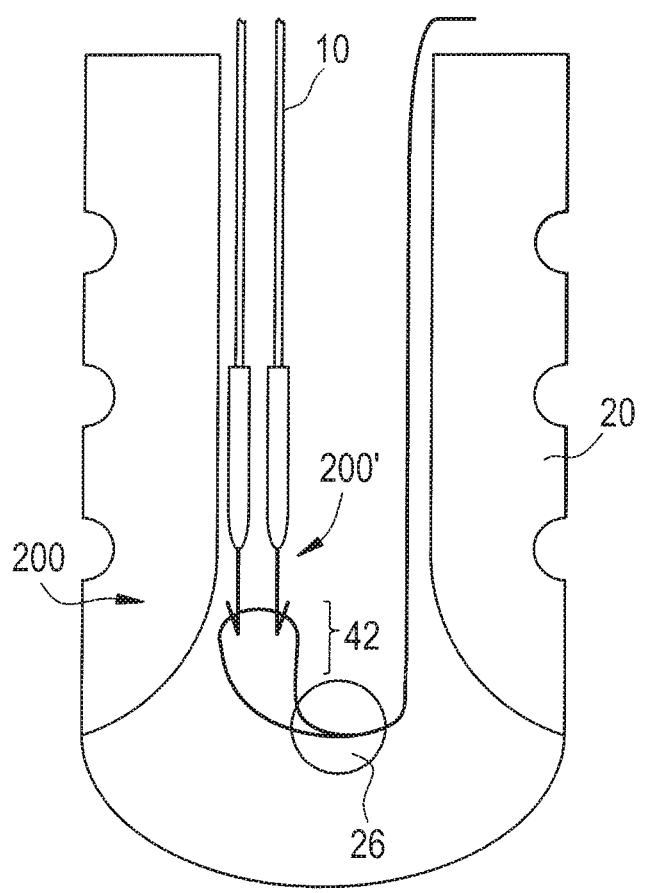
FIG. 10 is a perspective view of the suture leaders and threader of FIG. 9 being pulled through an eyelet of an anchor.

The suture 10 and leader 100 can be threaded through the anchor 20 in various ways and using various tools known in the art, such as a threader loop. As shown in FIG. 8, in general, the leader 100 can be bent into a 180° fold prior to being pulled through a lumen in a suture anchor, and the leader 100 can guide the suture therethrough. This can eliminate the need to fold the suture and pull the folded portion of the suture through the lumen of the anchor. In particular, when the suture leader 200 includes the pre-formed crease 204, the end portion of the leader 200 can be hooked onto a head portion 42 of the threader loop 40 prior to threading the leader 200 and the suture coupled thereto through the anchor. The leader 200 can be mated to the threader loop 40 in other ways, such as using a knot, glue, or other known engagement techniques. In another embodiment, shown in FIG. 9, when two suture leaders 200, 200' are coupled to a single strand of suture, the two suture leaders 200, 200' can be mated with a single threader loop 40. When the threader loop 40 or other threading tool is used, the threader loop 40 can be pre-disposed within the suture anchor 20 such that leading and trailing ends of the threader 40 extend from the proximal end 20p of the anchor 20. This allows the suture leader(s) 200, 200' to be hooked onto the head of the threader 40 and then simply pulled through the anchor 20. More specifically, during loading of the threader loop 40 onto the anchor 20, the threader loop 40 can extend distally through the cannulated portion of the anchor 20 and can be wrapped around or extend through the suture-receiving member 26, and can extend proximally back through the lumen and out of the proximal end of the anchor 20. A threader loop 40 loaded onto the anchor 20 is shown in FIG. 9, along with the suture leaders 200, 200' mated with first and second ends of a suture strand 10. In use, a pulling force can be applied to the leading end of the threader loop 40, which can pull the head 42 of the threader 40 (which is trailing) through the lumen of the anchor 20. The pulling force can cause the suture leaders 200, 200' to radially contract around the suture 10. The pulling force applied to the threader loop 40 can pull the first and second suture leaders 200, 200' through the lumen 22 of the anchor 20. As shown in FIG. 10, where the suture-receiving member 26 is an eyelet, the threader loop 40 can be pulled therethrough, along with the suture leaders 200, 200'. The applied pulling force can cause the suture leaders 200, 200' to radially contract around the suture 10 so that the leaders 200, 200' are sized to pass through the eyelet 26.

Figure 11:
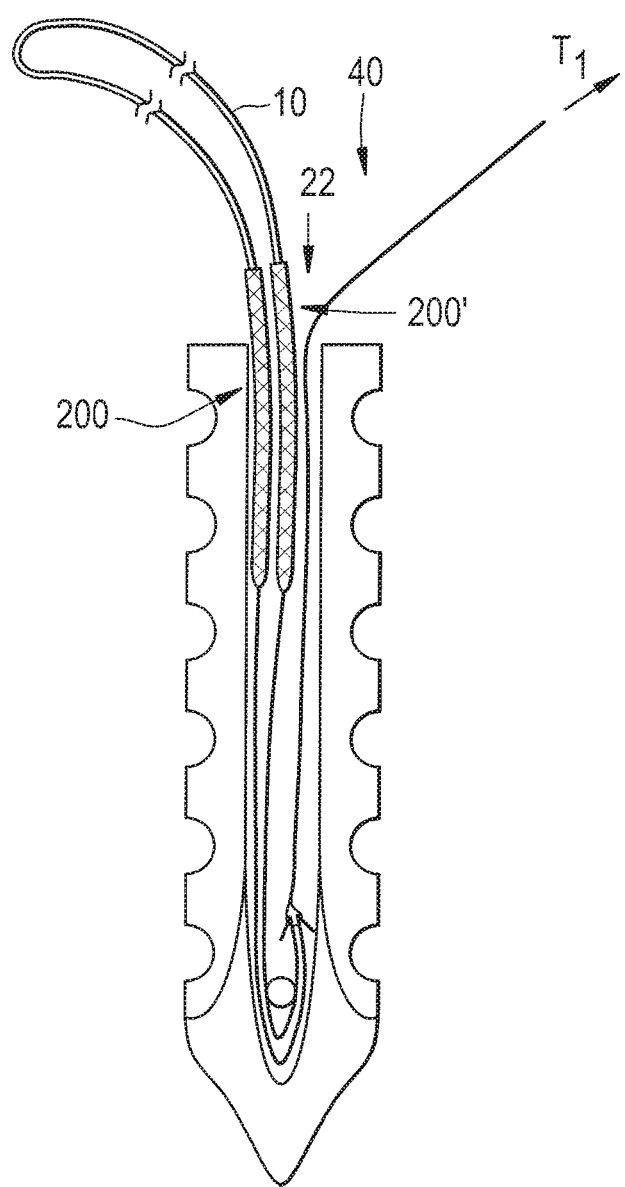
FIG. 11 is a cross-sectional view of the anchor of FIG. 7 with the suture leader of FIG. 3A threaded within the anchor.

FIG. 11 shows the leaders 200, 200' and the suture 10 being threaded through the anchor 20. The leading ends of the leaders 200, 200' can be partially inserted through the anchor 20 and a pulling or tensioning force $T_1$ can be applied, such as using the threader loop. The leaders 200, 200' can have a length such that they can extend substantially through the inner lumen 22 of the anchor 22, as shown, or in other embodiments the leaders 200, 200' can extend partially through the lumen 22. In embodiments where the leaders 200, 200' are formed from a braided material, the leaders 200, 200' can compress around the suture 10 in the overlapping region R as the leaders are pulled. This can facilitate secure engagement of the suture. Moreover, the smooth transition between the leaders 200, 200' and the suture 10 can prevent snagging of the leader 200 in the anchor 20, such as around the suture-receiving member 26. Moreover, because the leaders 200, 200' can be bent or hooked, they can have a smaller width than a folded suture. This technique can thus prevent the need to fold the suture 10 and then pull the folded portion of the suture 10 through the lumen 22. Moreover, the relative diameters of the suture 10 and the leaders 200, 200' can allow the pre-bent leaders 200, 200' to more easily fit within the lumen 22 of the anchor 20. As previously mentioned, the outer diameter of the overlapping region can be less than two times the outer diameter of the strand of suture. The outer diameter of the leading end of the leader 200 can be smaller than the outer diameter of the suture strand 10, such as two times smaller. This can be advantageous when the suture leaders 200, 200' and the suture 10 are being threaded through the lumen 22 of the anchor 20, as shown. FIG. 12 shows the suture 10 threaded completely through the anchor 20 and the leaders positioned outside of the anchor, with the suture 10 extending around the suture-engaging member 26. Because the terminal ends 10a, 10b of the suture 10 are pulled through the anchor 20 using the leaders 200, 200', it is possible to thread the suture 10 around the suture-engaging member 26 while having a small diameter $D_L$ lumen relative to the diameter of the suture 10. A person skilled in the art will appreciate that a single leader can be used to pull multiple ends of one or more sutures.

In one embodiment, the leader 100 can be removed from the terminal end 10a of the suture 10 after the suture is threaded through a suture anchor. Removal can be achieved in various ways, such as by relieving any tension applied and grasping the trailing and of the leader to slide the leader off of the suture. Where the suture leader 100 and suture 10 are fixed at one or more discrete locations, such as with welds, a manual force can be sufficient to break the bonds to allow the suture 10 to be removed from the leader 100. Alternatively, the suture leader 100 can be removed from the suture 10 by cutting the suture 10 at a location distal to the leader 100.

With the suture 10 threaded through the suture anchor 20, the suture anchor 20 can be deployed into the bone using various techniques. For example, the suture anchor 20 can be positioned on a distal end of a driver, and the driver can be rotated to force the suture anchor through the bone, such as through the bone tunnel previously described. The suture 10 can be tensioned to draw the tissue toward the suture anchor 20 either prior to, during, or subsequent to driving the suture anchor 20 into the bone. When the suture anchor 20 is fully seated in the bone, it can extend at least through cortical bone or through cortical bone and cancellous bone. After the suture 10 is tensioned to pull the tissue toward the bone, trailing ends of the suture can be tied off or otherwise secured to maintain contact between the tissue and the bone.

One skilled in the art will appreciate further features and advantages of the invention based on the above-described embodiments. Accordingly, the invention is not to be limited by what has been particularly shown and described, except as indicated by the appended claims. Further, although the systems, devices, and methods provided for herein are generally directed to surgical techniques, at least some of the systems, devices, and methods can be used in applications outside of the surgical field. All publications and references cited herein are expressly incorporated herein by reference in their entirety.

What is claimed is:

1. A method for threading suture into a suture anchor, comprising
   positioning a threader loop within a crease pre-formed from an intersection of two linear portions in a suture leader such that the suture leader is hooked onto the threader loop; and
   pulling the threader loop to pull the suture leader through a lumen in a suture anchor, the suture leader having a suture attached to a first trailing end thereof and the suture leader collapsing around the suture as the suture leader is pulled through the suture anchor.

2. The method of claim 1, wherein pulling the suture leader causes at least a portion of the suture leader to radially collapse around the suture.

3. The method of claim 1, wherein pulling the threader loop comprises pulling the threader loop distally through the lumen, around a suture-receiving member in the suture anchor, and proximally through the lumen.

4. The method of claim 1, further comprising detaching the suture leader from the suture strand after the suture leader is pulled through the suture anchor.

5. The method of claim 1, further comprising, prior to pulling the threader loop through the suture anchor, positioning the threader loop within a crease pre-formed in a second suture leader, the second suture leader being attached to a second trailing end of the suture.

6. The method of claim 5, wherein pulling the threader loop decreases outer diameters of the first and second suture leaders such that the first and second suture leaders are dimensioned to pass through an eyelet formed in the suture anchor.

7. The method of claim 1, wherein the suture leader has a first suture and a second suture attached to the first trailing end thereof.

8. The method of claim 1, further comprising applying a force to a leading end of the suture leader to cause the first trailing end of the suture leader to contract and engage a leading end of the suture.

9. A method for threading suture into a suture anchor, comprising
   positioning a threader loop within a crease pre-formed in a first suture leader such that the first suture leader is hooked onto the threader loop, the first suture leader being attached to a first trailing end of a suture;
   positioning the threader loop within a crease pre-formed in a second suture leader, the second suture leader being attached to a second trailing end of the suture; and
   subsequently pulling the threader loop to pull the first and second suture leaders through a lumen in a suture anchor, each of the first and second suture leaders collapsing around the suture as the first and second suture leaders are pulled through the suture anchor.

10. The method of claim 9, wherein pulling the threader loop decreases outer diameters of the first and second suture leaders such that the first and second suture leaders are dimensioned to pass through an eyelet formed in the suture anchor.

11. A method for threading suture into a suture anchor, comprising
    engaging a threader loop with a suture leader by placing the threader loop into a hook-shaped portion pre-formed on the suture leader; and
    pulling the threader loop to pull the suture leader through a lumen in a suture anchor, a trailing end of the suture leader engaging a leading end of a suture such that pulling the threader loop causes the suture leader to constrict onto the leading end of the suture and not pulling the threader loop causes the suture leader to loosen on the leading end of the suture.

12. The method of claim 11, wherein pulling the threader loop comprises pulling the threader loop distally through the lumen, around a suture-receiving member in the suture anchor, and proximally through the lumen.

13. The method of claim 11, further comprising detaching the suture leader from the suture after the suture leader is pulled through the suture anchor.

14. The method of claim 11, further comprising, prior to pulling the threader loop through the suture anchor, positioning the threader loop within a crease pre-formed in a second suture leader, the second suture leader being attached to a trailing end of the suture.

15. The method of claim 14, wherein pulling the threader loop decreases outer diameters of the first and second suture leaders such that the first and second suture leaders are dimensioned to pass through an eyelet formed in the suture anchor.

16. The method of claim 11, wherein the suture leader has a first suture and a second suture attached to the first trailing end thereof.

* * * * *